(12) United States Patent
Xie

(10) Patent No.: US 7,332,621 B2
(45) Date of Patent: Feb. 19, 2008

(54) PROCESS FOR PREPARING TAMSULOSIN

(75) Inventor: Meihua Xie, JiangSu Province (CN)

(73) Assignee: Scinopharm Taiwan Ktd. (TW)

( * ) Notice: Subject to any disclaimer, the term of this patent is extended or adjusted under 35 U.S.C. 154(b) by 0 days.

(21) Appl. No.: 11/644,328

(22) Filed: Dec. 22, 2006

(65) Prior Publication Data

US 2007/0142669 A1    Jun. 21, 2007

Related U.S. Application Data

(62) Division of application No. 11/201,878, filed on Aug. 11, 2005, now abandoned.

(30) Foreign Application Priority Data

Aug. 11, 2005  (CN) .................. 2004 1 0058397

(51) Int. Cl.
 *C07C 305/00* (2006.01)
 *C07C 315/00* (2006.01)
(52) U.S. Cl. .............. 558/37; 568/28; 568/33
(58) Field of Classification Search .......... None
 See application file for complete search history.

(56) References Cited

U.S. PATENT DOCUMENTS 2,825,736 A * 3/1958 Cope et al. .............. 558/48

4,731,478 A    3/1988 Niigata et al.

FOREIGN PATENT DOCUMENTS

| EP | 0 034 432 | 8/1981 |
|---|---|---|
| EP | 0 257 787 | 3/1988 |
| JP | 2000-229901 | 8/2000 |
| WO | 03/035608 | 5/2003 |
| WO | 03/037850 | 5/2003 |
| WO | 2004/016582 | 2/2004 |
| WO | 2004/022532 | 3/2004 |
| WO | 2004/087623 | 10/2004 |

OTHER PUBLICATIONS

Wheeler, W.J. "The Synthesis of the $^{14}$C and $^2$H-isotopomers of (R)-N[2'-ethoxyphenoxy)-ethyl]-N-2-(4'methoxy-3'-sulfonamido)-phenyl]-propylamine hydrochloride . . . " *Journal of Labelled Compounds and Radiopharmaceuticals* (1988) vol. XXVII, No. 2, pp. 171-180.

* cited by examiner

*Primary Examiner*—Sikarl A. Witherspoon
(74) *Attorney, Agent, or Firm*—Ladas & Parry LLP

(57) ABSTRACT

The present invention relates to a process for preparing Tamsulosin, an anti-benign prostatic hyperplasia drug, which comprises converting o-ethoxyphenoxyethanol to a corresponding sulfonate, and reacting the sulfonate with (R)-(−)-5-(2-aminopropyl)-2-methoxybenzenesulfonamide by condensation to produce Tamsulosin.

6 Claims, No Drawings

PROCESS FOR PREPARING TAMSULOSIN

This application is a divisional of copending application number 11/201,878 filed Aug. 11, 2005 now abandoned claims the benefit thereof and incorporates the same by reference.

FIELD OF THE INVENTION

The present invention relates to a process for preparing Tamsulosin, an anti-benign prostatic hyperplasia drug.

DESCRIPTION OF THE PRIOR ART

The chemical name of Tamsulosin is (R)-(−)-5-[2-[[2-(2-ethoxyphenoxy)ethyl]amino]propyl]-2-methoxybenzene-sulfonamide hydrochloride, with the following structural formula (1):

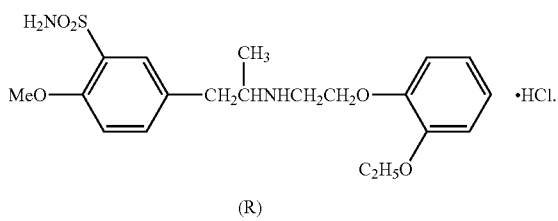

Tamsulosin is a selective antagonist of $\alpha_{1c}$-receptor, which was clinically used for treating hypertension initially, and now is mainly used for treating benign prostatic hyperplasia. Tamsulosin was developed by Yamanouchi Pharmaceutical Co., Ltd. of Japan and firstly commercialized in Japan in 1996. Yamanouchi Pharmaceutical Co. Ltd. owns a patent, EP 0 034 432 (published on Aug. 26, 1981), for Tamsulosin.

EP 0 034 432 to Imai et al. discloses a synthetic route of Tamsulosin as follows:

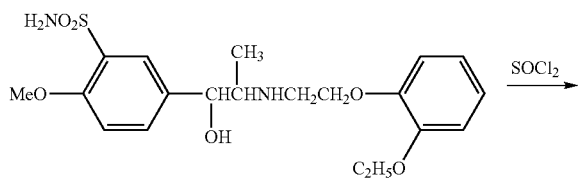

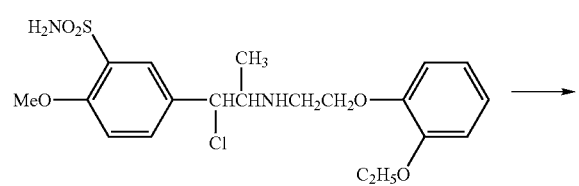

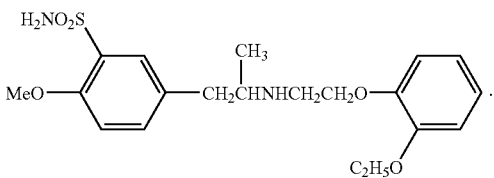

EP 0 257 787 to Okada et al. (published on Mar. 2, 1988) and U.S. Pat. No. 4,731,478 to Niigata et al. (published on Mar. 15, 1988) disclose that Tamsulosin is prepared, with a yield of approximately 40%, by condensation of R-(−)-5-(2-aminopropyl)-2-methoxybenzenesulfonamide with 1-bromo-2(o-ethoxyphenoxy)ethane. The synthetic route is as follows:

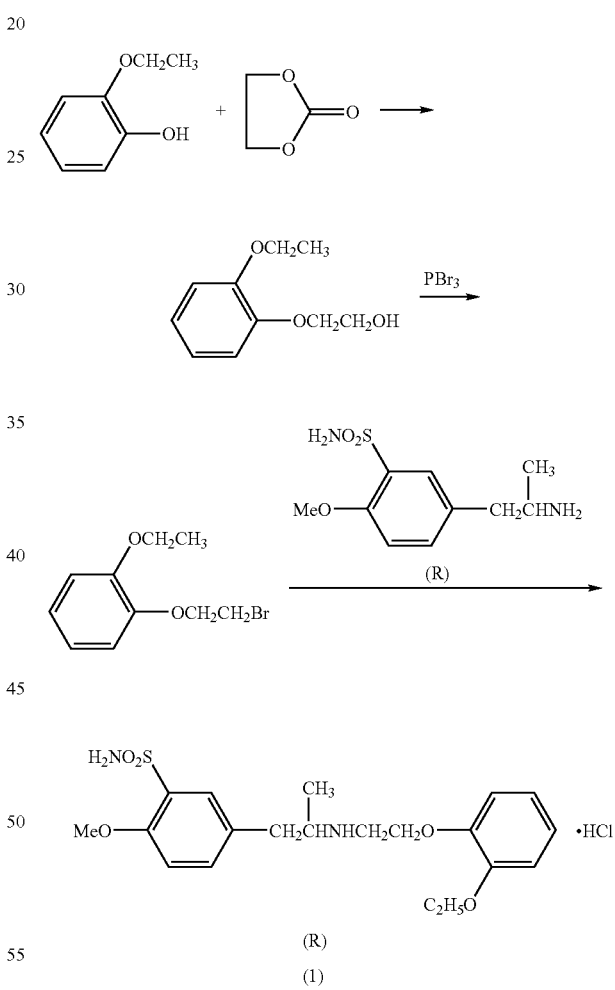

J of Labeled Compounds and Radiopharmaceuticals (I), 171 (1988) by William J. Wheler discloses that Tamsulosin is prepared by condensation of 2-(2-ethoxyphenoxy)-acetaldehyde with R-(−)-5(2-aminopropyl)-2-methoxybenzene-sulfonamide and followed by reduction. In the reaction, the use of 5% Pd/C can obtain a reduction yield of 32.8%, and the use of $NaBH_3CN$ can obtain a reduction yield of 57.2%.

The synthetic route is as follows:

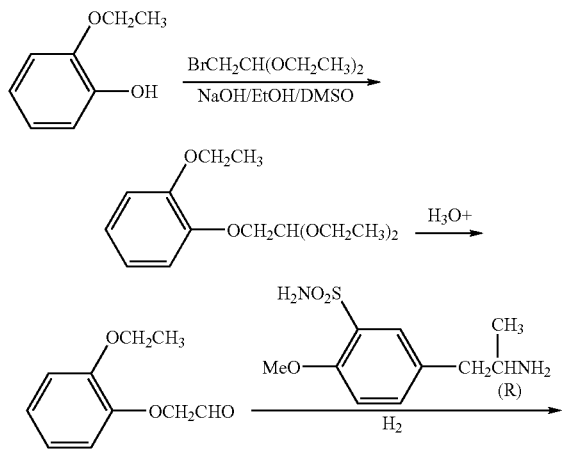

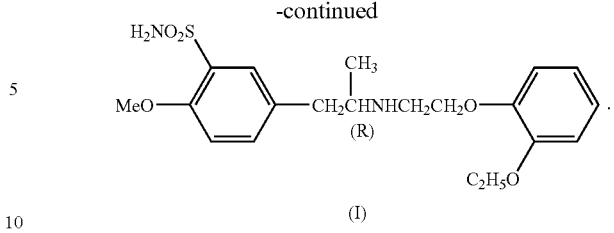

WO 03/037850 A1 to Hoorn et al. (published on May 8, 2003) discloses that Tamsulosin is prepared by condensation of 2-methoxy-5-(2-oxopropyl)-benzenesulfonamide with 2-(2-ethoxyphenoxy)-1-ethanamine and followed by reduction to afford DL-Tamsulosin, which is then salified with (+)camphor-10-sulphonic acid, resolved into individual optical isomers, and then recrystallized four times to produce Tamsulosin, with a yield of 8.9%. The synthetic route is as follows:

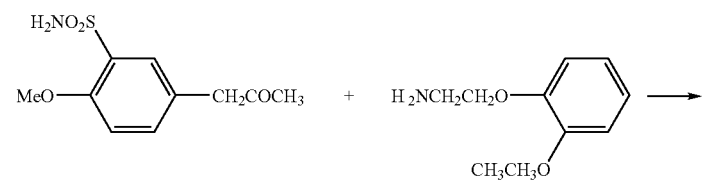

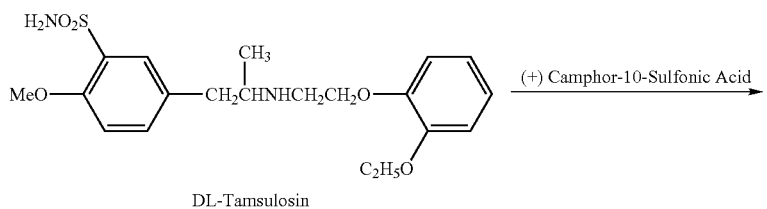

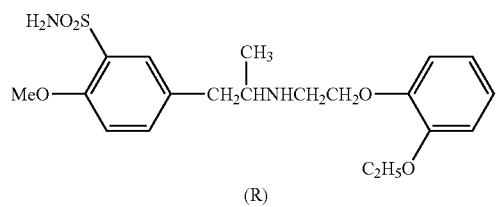

SUMMARY OF THE INVENTION

The present invention relates to a novel process for preparing Tamsulosin, which includes reacting o-ethoxyphenoxyethanol with sulfonyl chloride to produce a sulfonate, and then condensating the resulted sulfonate with an optically active amine, (R)-(−)-5-(2-aminopropyl)-2-methoxybenzenesulfonamide to produce Tamsulosin. The synthetic route is as follows:

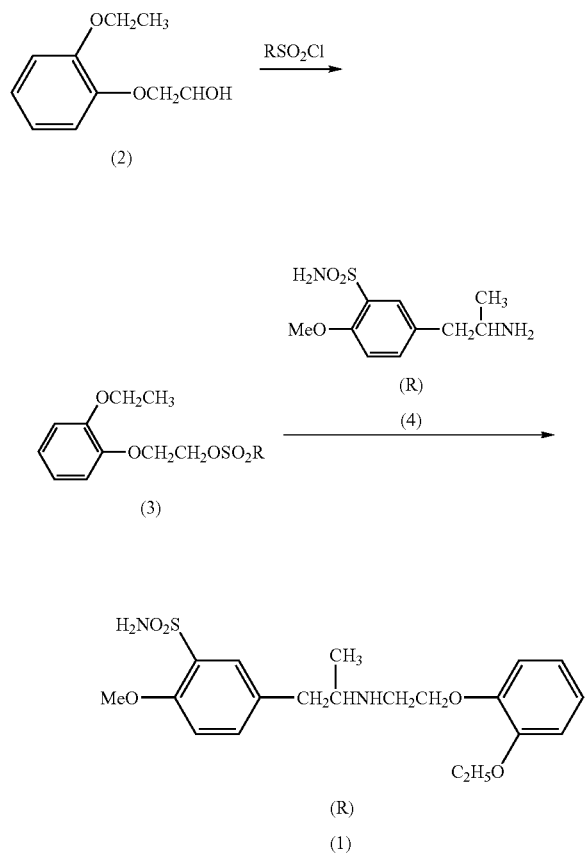

DETAILED DESCRIPTION OF THE INVENTION

The present invention relates to a novel process for preparing Tamsulosin, which includes reacting o-ethoxyphenoxyethanol with sulfonyl chloride to produce a sulfonate, and then condensating the resulted sulfonate with an optically active amine, (R)-(−)-5-(2-aminopropyl)-2-methoxybenzenesulfonamide to produce Tamsulosin. The synthetic route is as follows:

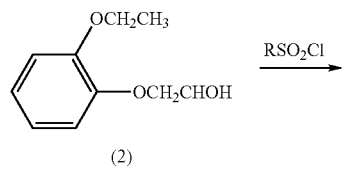

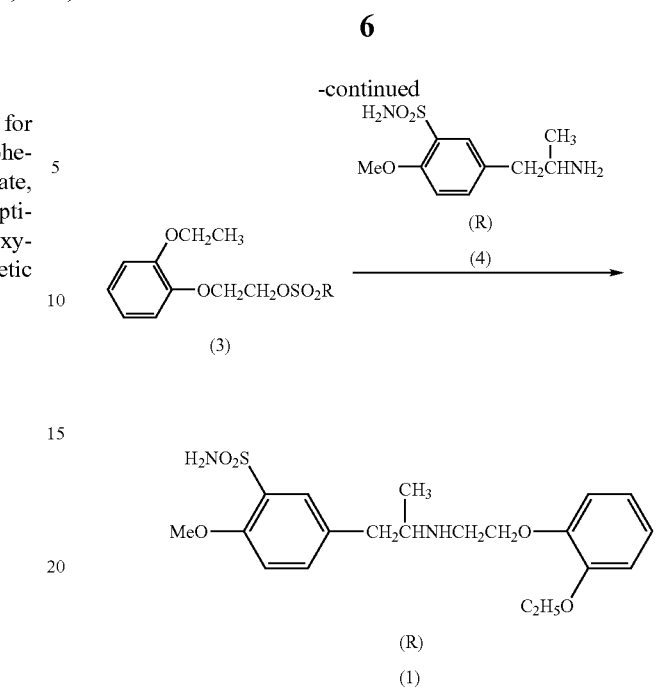

Specifically, the process of the present invention includes the following two steps: (i) reacting o-ethoxyphenoxyethanol (compound (2)) with sulfonyl chloride of Formula $RSO_2Cl$ to produce o-ethoxyphenoxyethanol sulfonate (compound (3)), wherein R is $(C_1\text{-}C_6)$alkyl, such as methyl and ethyl, or phenyl substituted by halogen, nitro and/or $(C_1\text{-}C_6)$alkyl (such as methyl), preferably substituted at the ortho, para, or meta position; and (ii) reacting the compound (3) with (R)-(−)-5-(2-aminopropyl)-2-methoxybenzenesulfonamide (compound (4)) with a suitable organic amine and/or inorganic base as an acid scavenger at a temperature of about 40 to 100° C., in the presence of a catalyst and a suitable solvent, to prepare Tamsulosin.

The detailed reaction steps and conditions are described as follows:

Step (i):

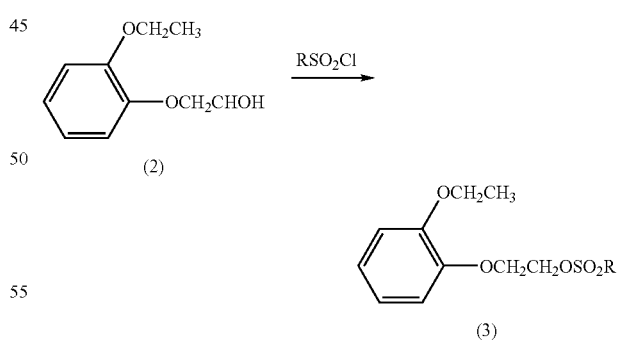

The compound (2) is dissolved into an organic solvent (the suitable solvent is selected from the group consisting of chloromethane (preferably dichloromethane and/or trichloromethane), chloroethane (preferably dichloroethane), benzene, substituted benzene (preferably toluene), pyridine, other similar organic solvents and mixtures thereof, stirred until they are fully dissolved, and cooled to about −10 to 10° C., preferably about −5 to 5° C., more preferably about −5 to 0° C. Then, sulfonyl chloride of Formula $RSO_2Cl$ (wherein R is $(C_1-C_6)$alkyl, such as methyl and ethyl, or phenyl substituted by halogen, nitro and/or $(C_1-C_6)$alkyl (such as methyl), preferably substituted at the ortho, para, and meta position) is added dropwise into the mixture. After addition, the reaction is carried out at a temperature of about 0 to 10° C., preferably about 0 to 5° C., until the compound (2) disappears. The reacting solution is gradually added into ice water to isolate white solids, which are then filtered, washed and dried to obtain the corresponding sulfonate (compound (3)), with a yield of 65-90%.

Step (ii)

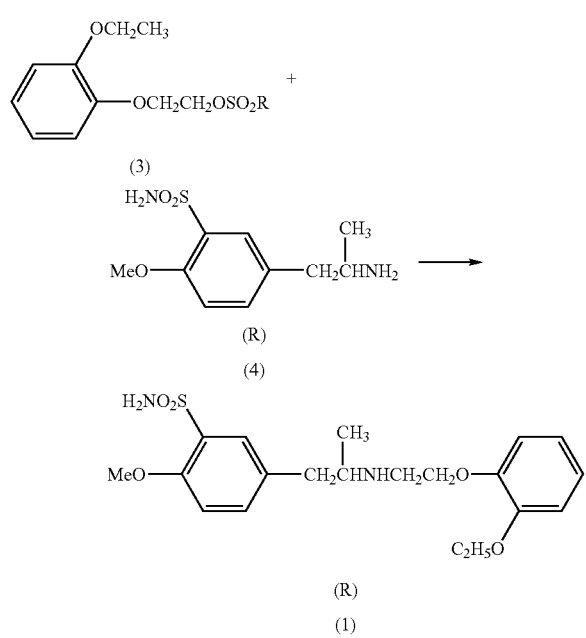

The compound (3), an organic amine and/or inorganic base as an acid scavenger, a catalyst and a suitable solvent are added into a reaction flask and heated to about 40-50° C., and then the compound (4) is added in portions; wherein the organic amine as an acid scavenger is selected from the group consisting of an organic tertiary amine, pyridine and mixtures thereof, preferably the group consisting of triethylamine, pyridine and mixtures thereof, and the inorganic base as an acid scavenger is selected from the group consisting of KOH, NaOH, $K_2CO_3$, $NaHCO_3$, the like and mixtures thereof; the catalyst is selected from the group consisting of monovalent inorganic iodides, preferably the group consisting of potassium iodide (KI), sodium iodide (NaI), copper iodide (CuI) and mixtures thereof; the proper solvent is an aprotic organic solvent, preferably selected from the group consisting of N,N-dimethylformamide (DMF), dimethyl sulphoxide (DMSO), N,N-dimethylacetamide (DMAC), the like and mixtures thereof. After the addition of the compound (4), the reaction mixture is heated at a temperature of about 50-100° C., preferably about 50-80° C., more preferably about 55-65° C., until the compound (3) disappears. Then, the mixture is cooled to room temperature, added with water, extracted with ethyl acetate or the like, distilled off the solvent under reduced pressure, and added with an organic solvent containing HCl (preferably selected from the group consisting of ethyl acetate-HCl, $CH_3OH$—HCl, EtOH—HCl, $(CH_3)_2CHOH$—HCl and mixtures thereof) to isolate white solids, which are then recrystallized with an aqueous methanol, various aqueous, alcohols, acetone, or dissolvants of above in mixture with ethyl acetate, methyl tert-butyl ether, benzene and/or toluene to produce Tamsulosin, with a yield of 55-70%.

EXAMPLES

Example 1 o-ethoxyphenoxyethanol-methylsulfonate 50.0 g (0.28 mol) o-ethoxyphenoxyethanol and 197 g pyridine are added into a reaction flask, stirred until they are fully dissolved, and then cooled to −5 to 0° C. During stirring, 53.1 g (0.46 mol) methyl sulfonyl chloride is added gradually into the flask at a temperature controlled at −5 to 0° C. After addition, the reaction lasts for 3 to 4 hours at a temperature of 0 to 5° C. After the reaction is complete, the reacting solution is added gradually into 350 ml ice water under stirring at a temperature controlled at 0 to 5° C. to isolate gradually white solids, which are then filtered, and the filter cake is rinsed three times with 150 ml water until there is no smell of pyridine, and then dried to obtain 61.9 g title compound. Yield: 85.0%; purity: 99.83% (HPLC).

Example 2

(R)-(−)-5-[2-[(2-ethoxyphenoxy)ethyl]amino]-propyl-2-methoxybenzenesulfonamide hydrochloride (Tamsulosin)

27.7 g (0.11 mol) o-ethoxyphenoxyethanol-methylsulfonate, 20.0 g (0.082 mol) R-(−)-5-(2-aminopropyl)-2-methoxybenzenesulfonamide, 7.5 g (0.09 mol) $NaHCO_3$, 1.36 g potassium iodide(KI) and 80 ml dimethylformamide (DMF) are placed into a reaction flask, which is supplied with $N_2$, heated to 55 to 65° C. and reacted for 11 hours. After the reaction is complete, the reacting solution is cooled to room temperature, added with 600 ml water, and extracted three times with 500 ml ethyl acetate. Then, the ethyl acetate extract solutions are combined, rinsed twice with 100 ml water, dried with anhydrous magnesium sulfate, and distilled off ethyl acetate under reduced pressure. After that, the residue is dissolved in ethanol and filtered while it is still warm. The filtrate is cooled to room temperature, and EtOH—HCl is added gradually until the filtrate has a pH of 2. White solids are isolated. Thereafter, the solids are recrystallized with aqueous ethanol to isolate white crystals, which are then filtered, washed with ethanol, and dried to obtain 20.4 g title compound. Yield: 56.9%.

I claim:

1. A process for preparing o-ethoxyphenoxyethanol sulfonate, which comprises the following step:
reacting o-ethoxyphenoxyethanol of Formula (2) with sulfonyl chloride of Formula $RSO_2Cl$ at a temperature of about −10 to 10° C., to produce o-ethoxyphenoxy-ethanol sulfonate of Formula (3),

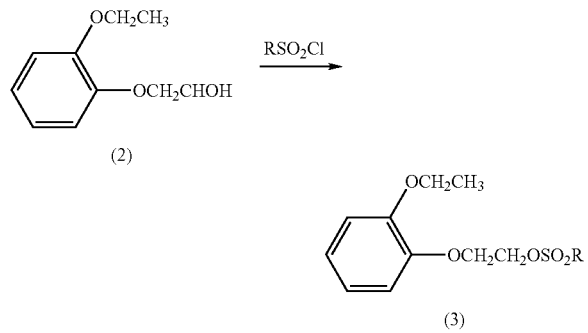

wherein R is $(C_1-C_6)$alkyl or phenyl substituted by halogen, nitro and/or $(C_1-C_6)$alkyl.

2. The process according to claim 1, wherein said reaction is conducted at a temperature of about −5 to 5° C.

3. The process according to claim 2, wherein said reaction is conducted at a temperature of about 0 to 5° C.

4. The process according to claim 1, wherein said reaction is conducted in the presence of a solvent.

5. The process according to claim 4, wherein said solvent is selected from the group consisting of chloromethane, chloroethane, benzene, substituted benzene, pyridine and mixtures thereof.

6. The process according to claim 5, wherein said solvent is selected from the group consisting of dichloromethane, trichloromethane, dichloroethane, benzene, toluene and mixtures thereof.

* * * * *

UNITED STATES PATENT AND TRADEMARK OFFICE
CERTIFICATE OF CORRECTION

| | |
|---|---|
| PATENT NO. | : 7,332,621 B2 |
| APPLICATION NO. | : 11/644328 |
| DATED | : February 19, 2008 |
| INVENTOR(S) | : Meihua Xie |

It is certified that error appears in the above-identified patent and that said Letters Patent is hereby corrected as shown below:

On title page, item 73, Assignee "Ktd." should read -- Ltd. -- and item 30 on title page, "11, 2005" should read -- 16, 2004 --.

Signed and Sealed this

Seventeenth Day of June, 2008

JON W. DUDAS
*Director of the United States Patent and Trademark Office*